United States Patent [19]

Burgess

[11] Patent Number: 4,463,016

[45] Date of Patent: Jul. 31, 1984

[54] METHOD FOR THE TREATMENT OF RAZOR BUMPS

[75] Inventor: Nelson L. Burgess, Bronx, N.Y.

[73] Assignee: Nel's Laboratory, Inc., Bronx, N.Y.

[21] Appl. No.: 421,474

[22] Filed: Sep. 22, 1982

[51] Int. Cl.³ .......................................... A61K 31/055
[52] U.S. Cl. ..................................................... 424/347
[58] Field of Search ........................................ 424/347

[56] References Cited

U.S. PATENT DOCUMENTS 4,228,163 10/1980 Bliss .................................... 424/240

OTHER PUBLICATIONS

Strauss et al., Arch. Dermatol., (1956), 74:533-42.
The Merck Manual, 10th ed., 1961, pp. 1440-1441.
The Merck Index, 9th ed., 1976, p. 279, para. 2165.

Primary Examiner—Leonard Schenkman
Attorney, Agent, or Firm—James H. Callwood

[57] ABSTRACT

The present disclosure is directed to a method of treating razor bumps which comprises administering to an individual suffering from razor bumps an effective amount of a 4-chloro-3,5-diloweralkylphenol compound in combination with a vehicle which facilitates topical application of said 4-chloro-3,5-diloweralkylphenol compound.

6 Claims, No Drawings

METHOD FOR THE TREATMENT OF RAZOR BUMPS

BACKGROUND OF THE INVENTION

1. Field of the Invention

The present invention is directed to a method for the treatment of razor bumps. More particularly, the present invention is directed to a method for treating razor bumps which comprises administering to an individual suffering from razor bumps an effective amount of a 4-chloro-3,5-diloweralkylphenol compound in combination with a vehicle which facilitates topical application.

2. Description of the Prior Art

Pseudofolliculitis of the beard (pseudofolliculitis barbae) more commonly known as "razor bumps" is an inflammatory state of the neck and chin which is characterized by erythematous lesions, firm papules and pustules containing buried hairs. While this affliction is known in Caucasions, it is essentially a condition which, in its most severe manifestations, is peculiar to the Negroid races. Strauss et al.: Pseudofolliculitis of the Beard; Arch. Dermatol (1956); 74:533–542.

The stated condition has been characterized by Strauss et al. supra as stemming from the curvy nature of Negroid hair which, upon growing out of the hair follicle, curves back in an arch and penetrates the skin.

The methodology of treatment disclosed in Strauss et al. suggests the use of depilatories such as barium sulfide powder or calcium thioglycollate for alleviation of symptoms of the condition. Additionally, Strauss et al. suggests that the topical application of such antibacterial agents as tetracycline or petrolatum produced insignificant long-term effects and that little is to be gained by combining antibacterial treatment with the use of depilatories.

One significant disadvantage of the use of depilatories is the fact that because they tend to irritate the skin, they can only be used infrequently by a substantial number of those persons who suffer from pseudofolliculitis, For example, Strauss et al. supra recommends that the depilatory be administered only once every three days to avoid irritation of the skin, and that even with this low frequency of administration, there was an occasional complaint regarding irritation.

For obvious reasons, the use of depilatories once every three days has significant drawbacks. For example, the growth of the beard which occurs during the three-day period could quite possibly cause an unkempt appearance. In accordance with the present invention, a methodology for treating "razor bumps" is described which avoids the problems of infrequent application and irritation associated with the prior art procedures.

SUMMARY OF THE INVENTION

A methodology for the treatment of razor bumps which comprises administering to an individual suffering from razor bumps an effective amount of a compound of the formula

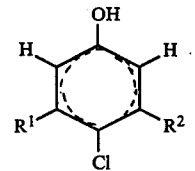

wherein $R^1$ and $R^2$ are $C_1$–$C_7$ straight- or branched-chain alkyl, in combination with a vehicle which facilitates topical application of the compound of formula I.

DETAILED DESCRIPTION OF THE INVENTION

As used throughout the specification and the appended claims, the term "alkyl" denotes a $C_1$–$C_7$ aliphatic hydrocarbon radical which may be straight- or branched-chain. Exemplary of alkyl are methyl, ethyl, propyl, isopropyl, butyl, secondary butyl, tertiary butyl, aryl, hexyl, heptyl and the like. The foregoing list of designations of alkyl is intended merely to provide exemplification and is intended to be non-limiting. The term "razor bumps" denotes the condition known as pseudofolliculitis barbae which is an inflammatory state of the neck, chin and jowl characterized by erythematous lesions, firm papules and pustules containing "buried" or "ingrown" hairs. It is recognized that the term "razor bumps" can also include other forms of pseudofolliculitis such as pseudofolliculitis capitae.

The compound of formula I may be administered to the chin, neck and jowl for the treatment of "razor bumps" in the form of a cream or a salve. Such a cream or salve would preferably contain the compound of formula I in concentrations in the range of from about 0.5% to 4.0% by weight of a compound of formula I in combination with a vehicle to make up a composition for topical application. Such a composition, in addition to containing an effective amount of a compound of formula I, would also preferably contain the following:

Purified or distilled water;

A moisturizing agent for retaining the water in the composition. Exemplary of a suitable moisturizing agent is propylene glycol;

A skin lubricant, e.g., lanolin;

A settling agent, e.g., sodium stearate;

A skin moisturizing agent, e.g., polyethylene glycol monostearate;

A skin lubricant such as sesame oil;

A skin moisturizer such as cetyl alcohol;

Antibacterial agents such as methyl benzoate and propyl benzoate;

An aseptic and anti-irritant agent such as camphor; and

A fragrance such as cucumber fragrance No. 24.

A preferred range of the compound of formula I in an antirazor bump composition is about 1.0% to 3.0% by weight, most preferably about 1.5% by weight.

Among the compounds generically encompassed by formula I, the compound 4-chloro-3,5-dimethylphenol (Entry No. 2165, Merck Index, 9th Edition) is most preferred as the active ingredient.

The invention is further exemplified by the following examples:

EXAMPLE I

Formulation Procedure

1. Place propylene glycol and purified water in a container and heat to 90° C. Then, dissolve sodium stearate and lanolin in appropriate proportions into solution.

2. In a separate container, add polyethylene glycol monostearate, 4-chloro-3,5-dimethylphenol, cetyl alcohol, methyl and propyl paraben, camphor and sesame oil. Heat to 170° F. Add fragrance.

Add "1." to "2." and mix well. Cool to 125° F. to 135° F. and fill in specified containers.

EXAMPLE II

1.5% Formulation

| Percent | | Weight |
|---|---|---|
| 35.0 | Propylene Glycol | 39.61 kg |
| 31.0 | Purified Water | 35.21 kg |
| 15.0 | Lanolin | 17.00 kg |
| 11.0 | Sodium Stearate | 12.50 kg |
| 2.0 | Polyethylene Glycol Monostearate | 2.30 kg |
| 2.0 | Sesame Oil | 2.30 kg |
| 1.5 | 4-Chloro-3,5-Dimethylphenol | 1.70 kg |
| .5 | Methyl Paraben | .568 kg |
| .2 | Propyl Paraben | .230 kg |
| .2 | Camphor | .230 kg |
| .5 | Cucumber Fragrance | .568 kg |
| 1.1 | Cetyl Alcohol | 1.42 kg |

EXAMPLE III

2.0% Formulation

| Percent | | Weight |
|---|---|---|
| 2.0 | 4-Chloro-3,5-Dimethylphenol | 2.26 kg |
| 30.75 | Purified Water | 34.92 kg |
| 14.75 | Lanolin | 16.71 kg |
| 35.0 | Propylene Glycol | 39.61 kg |
| 11.0 | Sodium Stearate | 12.50 kg |
| 2.0 | Polyethylene Glycol Monostearate | 2.30 kg |
| 2.0 | Sesame Oil | 2.30 kg |
| .5 | Methyl Paraben | .568 kg |
| .2 | Propyl Paraben | .230 kg |
| .2 | Camphor | .230 kg |
| .5 | Cucumber Fragrance | .568 kg |
| 1.1 | Cetyl Alcohol | 1.42 kg |

EXAMPLE IV

3.0% Formulation

| Percent | | Weight |
|---|---|---|
| 3.0 | 4-Chloro-3,5-Dimethylphenol | 3.40 kg |
| 30.25 | Purified Water | 34.23 kg |
| 14.25 | Lanolin | 16.15 kg |
| 35.0 | Propylene Glycol | 39.61 kg |
| 11.0 | Sodium Stearate | 12.50 kg |
| 2.0 | Polyethylene Glycol Monostearate | 2.30 kg |
| 2.0 | Sesame Oil | 2.30 kg |
| .5 | Methyl Paraben | .568 kg |
| .2 | Propyl Paraben | .230 kg |
| .2 | Camphor | .230 kg |
| .5 | Cucumber Fragrance | .568 kg |
| 1.1 | Cetyl Alcohol | 1.42 kg |

What is claimed is:

1. A method for the treatment of razor bumps which comprises topically administering to an individual suffering from razor bumps an effective amount of a compound of the Formula:

$$\underset{\text{Cl}}{\underset{|}{\overset{\text{OH}}{\underset{R^1 \diagup \diagdown R^2}{\bigcirc}}}} \quad \text{I}$$

wherein $R^1$ and $R^2$ are $C_1$–$C_7$ alkyl in combination with a vehicle which facilitates topical application of the compound of Formula I.

2. The method according to claim 1 wherein $R^1$ and $R^2$ are methyl.

3. The method according to claim 2 wherein said effective amount of a compound of formula I is in the range of about 1.0% to 3.0% by weight.

4. The method according to claim 1 wherein said effective amount of a compound of formula I is in the range of about 1.0% to 3.0% by weight.

5. The method according to claim 4 wherein said effective amount of a compound of formula I is about 1.5% by weight.

6. The method according to claim 5 wherein said vehicle is composed of ingredients selected from the group consisting of propylene glycol, purified water, lanolin, sodium stearate, polyethylene glycol monostearate, sesame oil, cetyl alcohol, methyl paraben, propyl paraben, camphor and cucumber fragrance.

* * * * *